United States Patent
Shimizu

(10) Patent No.: US 9,795,321 B2
(45) Date of Patent: Oct. 24, 2017

(54) BED-LEAVING SENSOR AND BED-LEAVING DETECTION METHOD

(71) Applicant: SUMITOMO RIKO COMPANY LIMITED, Komaki-shi, Aichi (JP)

(72) Inventor: Atsuki Shimizu, Komaki (JP)

(73) Assignee: SUMITOMO RIKO COMPANY LIMITED, Komaki (JP)

( * ) Notice: Subject to any disclaimer, the term of this patent is extended or adjusted under 35 U.S.C. 154(b) by 106 days.

(21) Appl. No.: 14/862,846

(22) Filed: Sep. 23, 2015

(65) Prior Publication Data

US 2016/0007887 A1   Jan. 14, 2016

Related U.S. Application Data

(63) Continuation of application No. PCT/JP2014/063882, filed on May 26, 2014.

(30) Foreign Application Priority Data

Jun. 28, 2013   (JP) .................................. 2013-136942

(51) Int. Cl.
  *G08B 21/22*   (2006.01)
  *A61B 5/11*   (2006.01)
  (Continued)

(52) U.S. Cl.
  CPC ............ *A61B 5/1115* (2013.01); *G01L 1/205* (2013.01); *G08B 21/22* (2013.01); *G08B 29/185* (2013.01);
  (Continued)

(58) Field of Classification Search
  CPC ..... A61B 5/1115; A61B 5/1117; G08B 21/22; G08B 23/00; G08B 29/185; G01L 1/205
  (Continued)

(56) References Cited

U.S. PATENT DOCUMENTS

| 7,656,299 B2 * | 2/2010 | Gentry | .................. A61B 5/1113 340/562 |
| 2006/0028350 A1 * | 2/2006 | Bhai | ..................... A61B 5/1115 340/666 |

(Continued)

FOREIGN PATENT DOCUMENTS

| JP | 2001-057996 A | 3/2001 |
| JP | 2007-190269 A | 8/2007 |

(Continued)

OTHER PUBLICATIONS

Jan. 7, 2016 International Preliminary Report on Patetability issued in International Patent Application No. PCT/JP2014/063882.

(Continued)

*Primary Examiner* — Hung T Nguyen
(74) *Attorney, Agent, or Firm* — Oliff PLC

(57) ABSTRACT

A bed-leaving sensor for detecting bed-leaving by a user on a bed, including: a sitting position detection member that detects a sitting position of the user based on a detection value of a pressure sensor arranged on the bed; and a bed-leaving behavior detection member that detects bed-leaving behavior of the user with at least one of the following as a condition: (i) the sitting position being detected within a preset bed-leaving expectation region, (ii) a movement volume of a sitting position center of gravity which is a center of gravity of the sitting position exceeding a given threshold value within a given time, and (iii) the sitting position center of gravity moving toward a preset bed-leaving range.

10 Claims, 11 Drawing Sheets

(51) Int. Cl.
*G01L 1/20* (2006.01)
*G08B 29/18* (2006.01)
*A61B 5/103* (2006.01)
(52) U.S. Cl.
CPC ..... *A61B 5/1036* (2013.01); *A61B 2562/0247* (2013.01); *A61G 2203/34* (2013.01)
(58) Field of Classification Search
USPC ...... 340/573.4, 573.5, 665, 666; 5/600, 618; 177/45, 144
See application file for complete search history.

(56) References Cited

U.S. PATENT DOCUMENTS

| | | | |
|---|---|---|---|
| 2009/0260158 A1* | 10/2009 | Kazuno | A61B 5/1115 5/600 |
| 2010/0231376 A1 | 9/2010 | Hirose | |
| 2013/0146371 A1* | 6/2013 | Shih | G01G 19/445 177/144 |

FOREIGN PATENT DOCUMENTS

| | | |
|---|---|---|
| JP | 2007-313189 A | 12/2007 |
| JP | 2007-330336 A | 12/2007 |
| JP | 2009-039453 A | 2/2009 |
| JP | 2011-189137 A | 9/2011 |
| JP | 2011-245059 A | 12/2011 |
| JP | 2012-011174 A | 1/2012 |
| JP | 2012-029871 A | 2/2012 |
| JP | 2012-250046 A | 12/2012 |
| JP | 2013-031770 A | 2/2013 |

OTHER PUBLICATIONS

Jun. 24, 2014 International Search Report issued in International Patent Application No. PCT/JP2014/063882.

Aug. 29, 2016 Office Action issued in Japanese Patent Application No. 2013-136942.

* cited by examiner

BED-LEAVING SENSOR AND BED-LEAVING DETECTION METHOD

INCORPORATED BY REFERENCE

The disclosure of Japanese Patent Application No. 2013-136942 filed on Jun. 28, 2013, including the specification, drawings and abstract is incorporated herein by reference in its entirety. This is a Continuation of International Application No. PCT/JP2014/063882 filed on May 26, 2014.

BACKGROUND OF THE INVENTION

1. Field of the Invention

The present invention relates to a bed-leaving sensor that detects bed-leaving by a user on a bed, and a bed-leaving detection method.

2. Description of the Related Art

For example, in a hospital, nursing facility or the like, when a care receiver such as a physically disabled patient, an elderly person or the like who is in bed tries to get out from the bed by himself, there is a risk of tumbling or falling down. In light of that, examination has been done of aiding a care receiver with leaving the bed by using a bed-leaving sensor for detecting bed-leaving when the care receiver leaves the bed, and when it is detected by the bed-leaving sensor that the care receiver is leaving the bed, a caregiver is notified.

As this kind of bed-leaving sensor, in Japanese Unexamined Patent Publication No. JP-A-2012-29871, proposed is a bed-leaving sensor for which a pressure sensor is arranged on a bed, and when the body pressure of the user detected by the pressure sensor is a designated value or less, it determines that the person left the bed. Also, in Japanese Unexamined Patent Publication No. JP-A-2012-11174, proposed is a bed-leaving sensor for which a load sensor is provided at each leg part, and when the movement volume of the load center of gravity detected by those load sensors goes to a designated value or less, it determines that the person left the bed. However, with the bed-leaving sensors noted in JP-A-2012-29871 and JP-A-2012-11174, bed-leaving is detected after the user has completely left the bed, so the detection timing is slow, and there is the risk of an accident such as the person having fallen down or the like already having occurred when the caregiver rushed to check.

Meanwhile, in Japanese Unexamined Patent Publication No. JP-A-2007-313189, proposed is a movement discrimination device for detecting that the user has sat up based on the movement volume and movement direction of the user's body center of gravity. However, with the movement discrimination device noted in JP-A-2007-313189, since it is determined a person has left the bed only by the user sitting up, there is a high risk of false alarms, with bed-leaving detected even when it is simply sitting up unrelated to leaving the bed, and in addition to there being a high risk of false alarms, the detection timing is early, and there is a risk of the caregiver being called frequently.

SUMMARY OF THE INVENTION

The present invention has been developed in view of the above-described matters as the background, and it is an object of the present invention to provide a bed-leaving sensor with a novel structure and a bed-leaving detection method that is able to detect a user leaving the bed before bed-leaving is completed, and with good accuracy.

The above and/or optional objects of this invention may be attained according to at least one of the following aspects of the invention. The following aspects and/or elements employed in each aspect of the invention may be adopted at any possible optional combinations.

A first aspect of the present invention provides a bed-leaving sensor for detecting bed-leaving by a user on a bed, comprising: a sitting position detection member that detects a sitting position of the user based on a detection value of a pressure sensor arranged on the bed; and a bed-leaving behavior detection member that detects bed-leaving behavior of the user with at least one of the following as a condition: (i) the sitting position being detected within a preset bed-leaving expectation region, (ii) a movement volume of a sitting position center of gravity which is a center of gravity of the sitting position exceeding a given threshold value within a given time, and (iii) the sitting position center of gravity moving toward a preset bed-leaving range.

With the bed-leaving sensor according to the present invention, in the case of (i) the sitting position of the user being detected within a preset bed-leaving expectation region, it is possible to detect bed-leaving. Bed-leaving with the present invention includes bed-leaving behavior connected to bed-leaving. Also, the bed-leaving expectation region means a region on a bed for which it is assumed the buttocks of the user will be placed when the user is leaving the bed, and for example, it means an outer peripheral part of the bed, or, when a railing for preventing falling out of the bed is provided, it means the foot side area for which the railing is not provided. Also, with the present invention, bed-leaving is determined at the point that the user trying to leave the bed has taken a sitting position posture in a designated bed-leaving expectation region, and it is possible to detect bed-leaving before the user completely leaves the bed. In addition to that, since simply a sitting position does not mean bed-leaving is determined, it is possible to detect bed-leaving behavior with better precision, and it is possible to reduce the risk of false alarms.

Furthermore, in the case of (ii) the movement volume of the sitting position center of gravity which is the center of gravity of the sitting position exceeding a designated threshold value within a designated time, bed-leaving is detected. The user attempting to leave the bed sometimes moves on the bed in a sitting position posture having sat up, and with the present invention, by detecting that kind of action, it is possible to detect bed-leaving before the user leaves the bed. In addition, in the case of (iii) the sitting position center of gravity moving toward a preset bed-leaving range, bed-leaving is detected. The bed-leaving range is the bed edge range for which it is assumed the user will pass through when leaving the bed, and for example when a railing is provided at the edge of the bed, it means the edge for which the railing is not provided. By doing this, the movement of a user trying to leave the bed facing outside the bed is detected, and it is possible to detect the bed-leaving behavior of the user. In this way, with the bed-leaving sensor of the present invention, it is possible to detect the bed-leaving behavior of a user on a bed trying to leave the bed, so it is possible to detect bed-leaving before the user completely leaves the bed, and to detect bed-leaving with good precision.

A second aspect of the present invention provides the bed-leaving sensor according to the first aspect, wherein the bed-leaving expectation region is set to be a foot side region on the bed.

With this aspect, by setting the bed-leaving expectation region for detecting the sitting position of the user to be a foot side region of the bed at which the user's feet are positioned in a normal use state, it is possible to detect the sitting position of the user trying to leave the bed with good precision.

A third aspect of the present invention provides the bed-leaving sensor according to the first or second aspect, wherein the pressure sensor is arranged only at a bed-leaving possibility region on the bed.

The bed-leaving possibility region on the bed with this aspect is the region on the bed for which the user can get down from the bed, and means the region for which the outer circumference is open with the bed without being blocked by a railing, wall or the like. Also, with this aspect, it is possible to make the pressure sensor compact, and to ensure good sleep comfort for the user.

A fourth aspect of the present invention provides the bed-leaving sensor according to any one of the first through third aspects, wherein the sitting position detection member sets a determination area in a periphery of a pressure sensing center of a region in which pressure of a given contact threshold value or greater is detected within a preset sitting position determination region on the pressure sensor, and the sitting position is detected based on a ratio of a total pressure detected within the determination area occupying a total pressure detected within the sitting position determination region, a breadth of the region in which the pressure of the contact threshold value or greater is detected within the sitting position determination region, and the total pressure detected within the sitting position determination region.

With this aspect, by using the breadth of the region detected by the pressure sensor and the size of the pressure, it is possible to detect with good precision that the user is in the sitting position. Specifically, the size of the region for which pressure of the contact threshold value or greater is detected correlates to the buttocks, and by determining a person is in the sitting position when the size of the pressure is a size correlating to when pressure is focused on the buttocks by the sitting position, it is possible to distinguish between lying on one's back, lying on one's side, and the sitting position. The pressure sensing center can also be an item for which the center part of the region in which the pressure is detected can be roughly identified. For example, the pressure sensing center can be the center of gravity of the region for which the pressure is detected, or can be the area center of the region for which the pressure is detected.

A fifth aspect of the present invention provides the bed-leaving sensor according to the fourth aspect, wherein the pressure sensing center is a center of gravity of the region in which the pressure of the contact threshold value or greater is detected with the pressure sensor.

With this aspect, by using the center of gravity as the pressure sensing center, it is possible to identify the center part of the region for which an output value of the contact threshold value or greater is detected with good precision, and possible to increase the determination precision of the sitting position.

A sixth aspect of the present invention provides the bed-leaving sensor according to the fourth aspect, wherein the pressure sensing center is an area center of the region in which the pressure of the contact threshold value or greater is detected with the pressure sensor.

With this aspect, by using the area center as the pressure sensing center, it is possible to simplify the pressure sensing center calculation process, and it is possible to more quickly determine the sitting position.

A seventh aspect of the present invention provides the bed-leaving sensor according to any one of the first through sixth aspects, further comprising a notification member for notifying that the bed-leaving behavior of the user has been detected.

With this aspect, with the notification member, when the user on the bed is trying to leave the bed, it is possible to notify a caregiver or the like, for example. As the notification member, for example, it is possible to have a sound ring, to notify with a sound or warning light at a nurse station separated from the room in which the bed is equipped, or the like.

A first aspect of the present invention provides a bed-leaving detection method for detecting bed-leaving by a user on a bed, comprising: a sitting position detection step for detecting a sitting position of the user based on a detection value of a pressure sensor arranged on the bed; and a bed-leaving behavior detection step for detecting bed-leaving behavior of the user with at least one of the following as a condition: (i) the sitting position being detected within a preset bed-leaving expectation region, (ii) a movement volume of a sitting position center of gravity which is a center of gravity of the sitting position exceeding a given threshold value within a given time, and (iii) the sitting position center of gravity moving toward a preset bed-leaving range.

With the bed-leaving detection method according to the present invention, the same as with the bed-leaving sensor of the present invention described above, it is possible to detect bed-leaving behavior of a user trying to leave the bed with good precision before the user on the bed leaves the bed.

A second aspect of the present invention provides the bed-leaving detection method according to the first aspect, wherein a foot side region on the bed is set as the bed-leaving expectation region.

With this aspect, by setting the bed-leaving expectation region at which the sitting position of the user is detected to the foot side region of the bed at which the feet of the user are positioned in a state of normal use, it is possible to detect the sitting position of the user attempting to leave the bed with good precision.

A third aspect of the present invention provides the bed-leaving detection method according to the first or second aspect, wherein with the sitting position detection step, a determination area is set in a periphery of a pressure sensing center of a region in which pressure of a given contact threshold value or greater is detected within a preset sitting position determination region on the pressure sensor, and the sitting position is detected based on a ratio of a total pressure detected within the determination area occupying a total pressure detected within the sitting position determination region, a breadth of the region in which the pressure of the contact threshold value or greater is detected within the sitting position determination region, and the total pressure detected within the sitting position determination region. With this aspect, the same as with the bed-leaving sensor of the present invention described above, it is possible to detect the sitting position of the user with good precision.

With the bed-leaving sensor and the bed-leaving detection method according to the present invention, the determination of bed-leaving was set with at least one of the following as a condition: (i) the sitting position being detected within a designated bed-leaving expectation region, (ii) the sitting position center of gravity moving a designated value or greater, and (iii) the sitting position center of gravity movement direction being the movement direction during bed-leaving. By doing this, it is possible to detect leaving of the bed with good precision before the person trying to leave the bed completely leaves the bed.

BRIEF DESCRIPTION OF THE DRAWINGS

The foregoing and/or other objects, features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
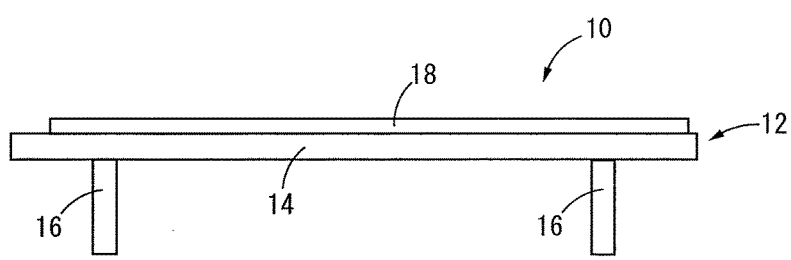
FIG. 1 is a side view of a bed equipped with a bed-leaving sensor of a first embodiment of the present invention.

Following, we will describe embodiments of the present invention while referring to the drawings.

Figure 2:
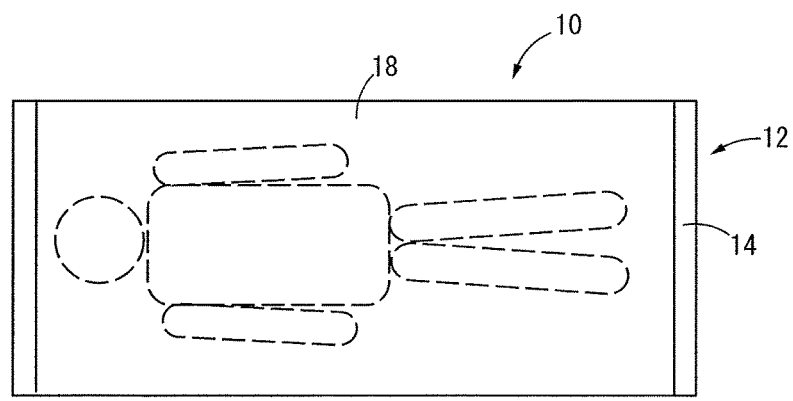
FIG. 2 is a top view of the bed shown in FIG. 1.

First, FIG. 1 and FIG. 2 show a bed 12 equipped with a bed-leaving sensor 10 of a first embodiment of the present invention. The bed 12 is constituted with a base board 14 for supporting a human body being supported by four leg parts 16. With the description hereafter, unless specifically noted, the vertical direction means the lateral direction in FIG. 1 which is the lengthwise direction of the bed 12, and the horizontal direction means the vertical direction in FIG. 2 which is the width direction of the bed 12.

Figure 3:
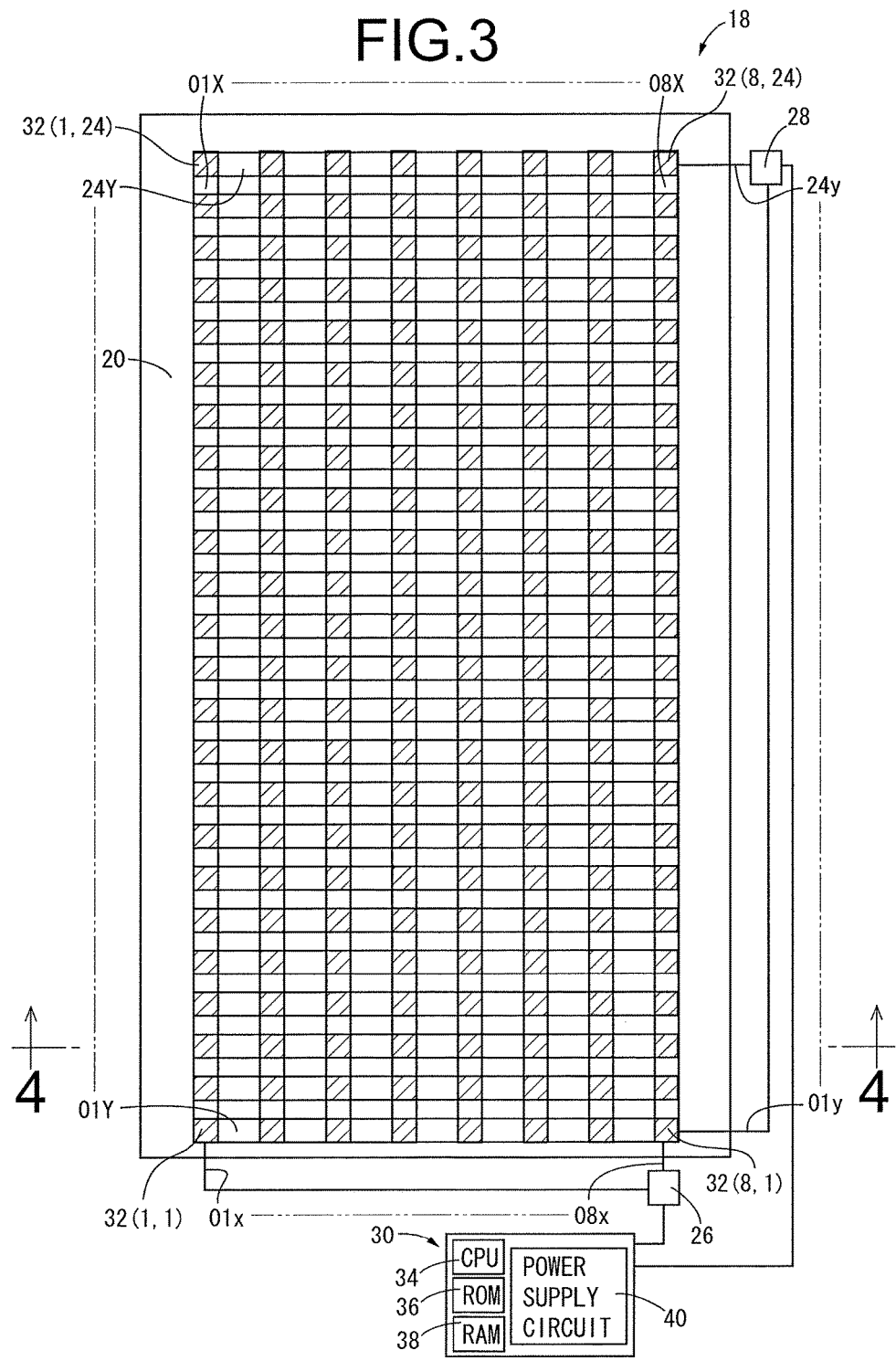
FIG. 3 is a top view of a pressure sensor provided on the bed shown in FIG. 1.
Figure 4:
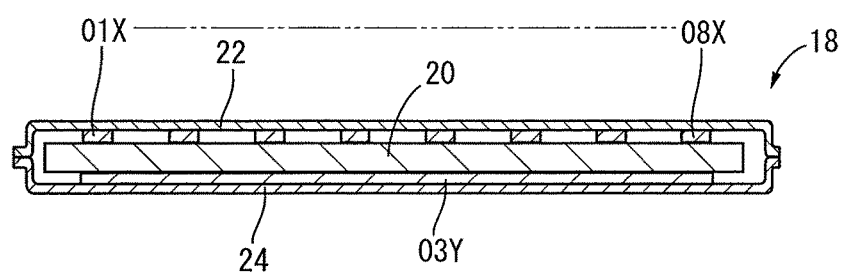
FIG. 4 is a cross section view taken along line 4-4 of FIG. 3.

A pressure sensor 18 is arranged on the base board 14 of the bed 12. The pressure sensor 18 is made to be a size that extends across roughly the entire surface of the base board 14. FIG. 3 and FIG. 4 schematically show the pressure sensor 18. In FIG. 3, to make it easier to understand, a dielectric layer 20 and front side base material 22 described later are illustrated as see-through, and pressure detectors 32 are shown with diagonal lines applied.

The pressure sensor 18 is equipped with the dielectric layer 20, front side electrodes 01X to 08X, back side electrodes 01Y to 24Y, front side wiring 01x to 08x, back side wiring 01y to 24y, front side base material 22, back side base material 24, front side wiring connector 26, and back side wiring connector 28, and the front side wiring connector 26 and the back side wiring connector 28 are electrically connected to a data processing device 30. The front side wiring 01x to 08x, the back side wiring 01y to 24y, the front side wiring connector 26, and the back side wiring connector 28 are all arranged within the pressure sensor 18, but in FIG. 3, to make visibility easier, they are shown schematically outside the pressure sensor 18.

The dielectric layer 20 is made of urethane foam as an elastomer, exhibits a sheet shape in a rectangular plate shape, and is elastically deformable. The dielectric layer 20 is of a size that covers roughly the entire surface of the base board 14 of the bed 12.

The front side base material 22 is made of rubber, and exhibits a rectangular plate shape. The front side base material 22 is laminated above (front side) the dielectric layer 20. The back side base material 24 is made of rubber, and exhibits a rectangular plate shape. The back side base material 24 is laminated below (back side) the dielectric layer 20.

As shown in FIG. 4, the outer edge of the front side base material 22 and the outer edge of the back side base material 24 are joined, and the front side base material 22 and the back side base material 24 are adhered together in bag form. The dielectric layer 20 is housed inside that bag. The top surface four corners of the dielectric layer 20 are adhered in spot form on the bottom surface four corners of the front side base material 22. Also, the bottom surface four corners of the dielectric layer 20 are adhered in spot form on the top surface four corners of the back side base material 24. In this way, the dielectric layer 20 is aligned so as not to have wrinkles occur during use on the front side base material 22 and the back side base material 24. However, the dielectric layer 20 is elastically deformable in the horizontal direction (front-back and left-right directions) in relation to the front side base material 22 and the back side base material 24 in a state with the four corners adhered.

A total of eight front side electrodes 01X to 08X are arranged on the top surface of the dielectric layer 20. The front side electrodes 01X to 08X are each formed including acrylic rubber and conductive carbon black. The front side electrodes 01X to 08X each exhibit a band shape and are formed so as to be able to expand and contract flexibly. The front side electrodes 01X to 08X each extend in the vertical direction (vertical direction in FIG. 3). The front side electrodes 01X to 08X are separated apart by a designated gap in the horizontal direction (lateral direction in FIG. 3), and are arranged to be roughly parallel to each other.

A total of eight front side wiring 01x to 08x are arranged on the top surface of the dielectric layer 20. The front side wiring 01x to 08x are each formed including acrylic rubber and silver powder. The front side wiring 01x to 08x each exhibit a linear shape. The front side wiring connector 26 is arranged at the corner part of the front side base material 22 and the back side base material 24. The front side wiring 01x to 08x each connect the front side electrodes 01X to 08X end parts with the front side wiring connector 26.

A total of 24 back side electrodes 01Y to 24Y are arranged on the bottom surface of the dielectric layer 20. The back side electrodes 01Y to 24Y are each formed including acrylic rubber and conductive carbon black. Each of the back side electrodes 01Y to 24Y exhibits a band shape, and are formed to be able to expand and contract flexibly. The back side electrodes 01Y to 24Y each extend horizontally (lateral direction in FIG. 3). The back side electrodes 01Y to 24Y are separated apart by a designated gap in the vertical direction (vertical direction in FIG. 3), and are arranged to be mutually roughly parallel. In this way, the front side electrodes 01X to 08X and the back side electrodes 01Y to 24Y are arranged in a mutually orthogonal matrix form when seen from above or from below.

A total of 24 back side wiring 01y to 24y are arranged on the bottom surface of the dielectric layer 20. The back side wiring 01y to 24y are each formed including acrylic rubber and silver powder. The back side wiring 01y to 24y each exhibit a linear form. The back side wiring connector 28 is arranged at the corner part of the front side base material 22 and the back side base material 24. The back side wiring 01y to 24y each connect the back side electrode 01Y to 24Y end parts with the back side wiring connector 28.

As shown by the squares to which diagonal lines are applied in FIG. 3, the plurality of pressure detectors 32 that the pressure sensor 18 is equipped with are arranged on the parts for which the front side electrodes 01X to 08X and the back side electrodes 01Y to 24Y intersect in the vertical direction (overlapping parts), and are arranged roughly equally vertically and horizontally across roughly the entire surface of the dielectric layer 20. The pressure detectors 32 are each equipped with a portion of the front side electrodes 01X to 08X, a portion of the back side electrodes 01Y to 24Y, and a portion of the dielectric layer 20. A total of 192 (=8×24) pressure detectors 32 are arranged. With the bed-leaving detection method described later which is executed with the bed-leaving sensor 10, each pressure detector 32, using the front side electrodes 01X to 08X as the x coordinate values and the back side electrodes 01Y to 24Y as the y coordinate values, are recognized as the pressure detectors 32 $(x, y)$. For example, the pressure detector 32 positioned at the lower left corner in FIG. 3 that is arranged at the intersecting part of the front side electrode 01X and the back side electrode 01Y is recognized as pressure detector 32 (1, 1), and the pressure detector 32 positioned at the upper right corner in FIG. 3 that is arranged at the intersecting part of the front side electrode 08X and the back side electrode 24Y is recognized as pressure detector 32 (8, 24).

As shown in FIG. 3, the data processing device 30 is equipped with a CPU (Central Processing Unit) 34, a ROM (Read Only Memory) 36, a RAM (Random Access Memory) 38, and a power supply circuit 40. Stored in the ROM 36 are a detection program shown in FIG. 6 based on the bed-leaving detection method described later, a map indicating the correspondence between the electrostatic capacity of the capacitor constituted by the pressure detectors 32 and the body pressure (load). In the RAM 38, temporarily stored are the calculation values of the detection program, or the output values of the electrostatic capacitance of the pressure detectors 32 input from the front side wiring connector 26 and the back side wiring connector 28. Also, the power supply circuit 40 applies in scanning sequence the periodic square wave voltage to the pressure detectors 32. Then, from the electrostatic capacitance of the pressure detectors 32 stored in the ROM 36, based on the map stored in the ROM 36, the CPU 34 is made to detect body pressure acting on the pressure detectors 32.

As shown in FIG. 1 and FIG. 2, the pressure sensor 18 constituted in this way is overlapped on the base board 14 of the bed 12. Then, when the user lies down on the pressure sensor 18, the body load (body pressure) based on gravity acting on the user is applied to the plurality of pressure detectors 32 of the pressure sensor 18.

Figure 5:
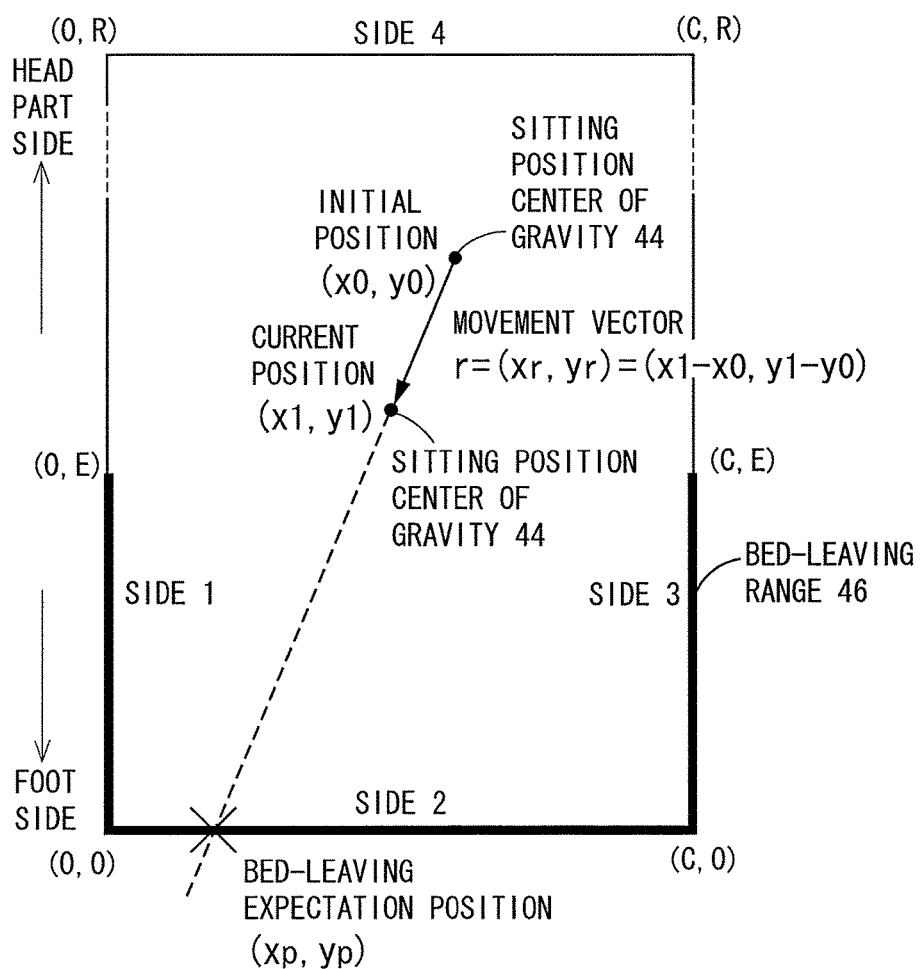
FIG. 5 is an explanatory diagram for describing a bed-leaving detection method of a first embodiment of the present invention.

Next, we will describe in advance a summary of the first embodiment of the present invention as the bed-leaving detection method executed with this kind of data processing device 30 of the bed-leaving sensor 10 while referring to FIG. 5. FIG. 5 shows the movement of a sitting position center of gravity 44 of the user on the pressure sensor 18, where the upper part of the drawing is the head part side of the bed 12, and the lower part of the drawing is the foot side of the bed 12. In FIG. 5, to make calculation of the bed-leaving expectation position $(x_p, y_p)$ described later easy, the origin point is set to (0, 0), so as necessary, a correction such as calculating the sitting position center of gravity 44 after subtracting 1 at a time respectively for the x coordinate and the y coordinate of the coordinate value of the pressure detector 32 with the origin point as (1, 1), or subtracting 1 each respectively for the x coordinate and the y coordinate of the sitting position center of gravity 44 after calculating the sitting position center of gravity 44, is performed. With this embodiment, when a designated threshold value has been exceeded by the movement volume: |r| of the sitting position center of gravity 44 of the user within a designated time, or when the sitting position center of gravity 44 moves toward a preset bed-leaving range 46, this is determined to be bed-leaving behavior. The bed-leaving range 46 is the range of the edge of the bed 12 assumed that the user will pass through when leaving the bed, and with this embodiment, is set to be the edge of the foot side of the bed 12. Also, R in FIG. 5 is the number of pressure detectors 32 in the vertical direction of the bed 12, and C is the number of pressure detectors 32 in the horizontal direction of the bed 12.

Figure 6:
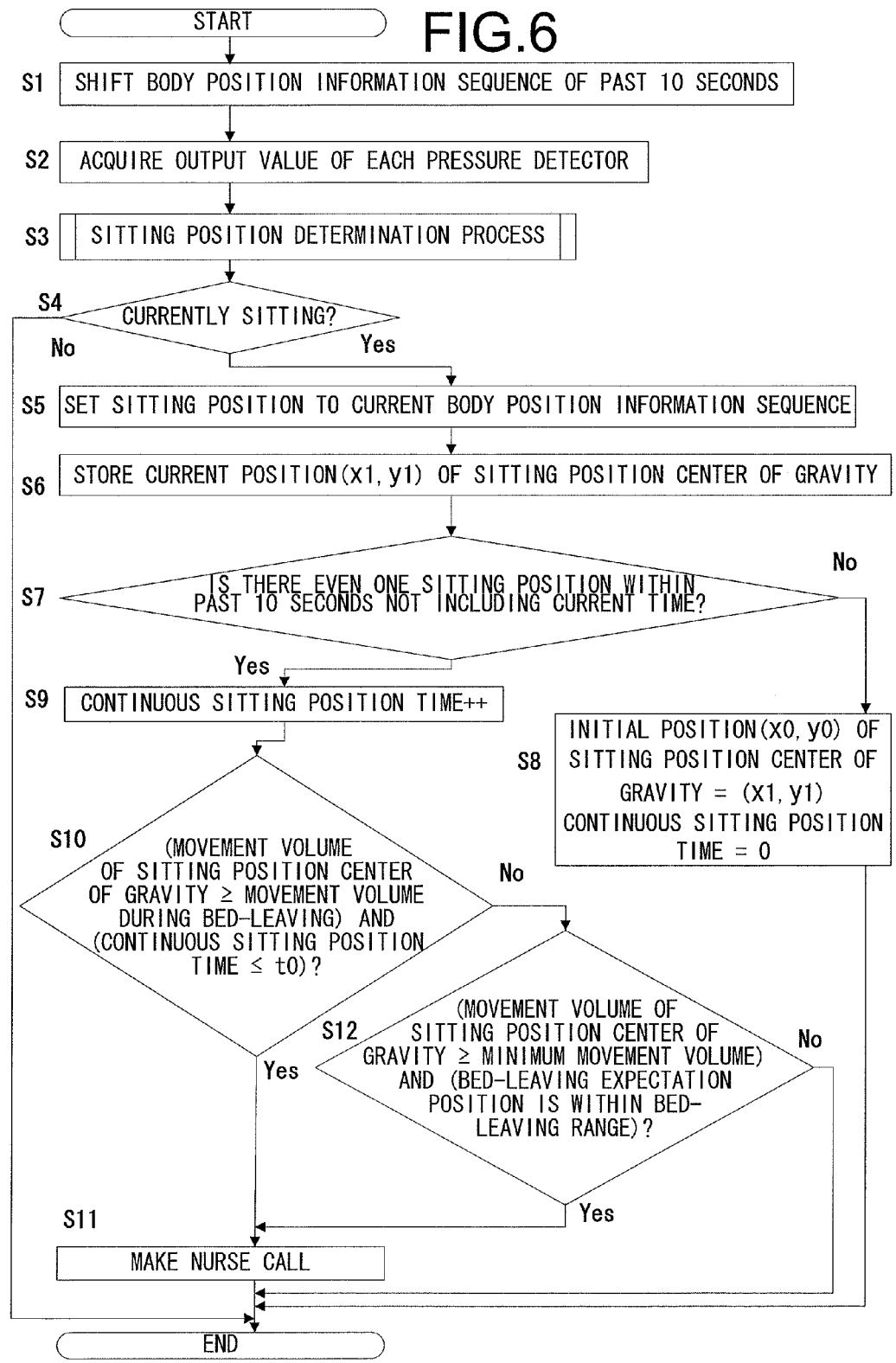
FIG. 6 is a flow chart showing the bed-leaving detection method of the first embodiment of the present invention.

FIG. 6 shows the processing contents executed by the CPU 34 of the data processing device 30. This process is repeatedly executed every designated interval of 0.05 seconds to 1 second, for example. First, at S1, the CPU 34 shifts the body position information sequence of the past 10 seconds. For the body position information sequence, body position information indicating a detected body position such as lying on one's back, lying on one's side, a prone position, a sitting position or the like is stored for the past 10 seconds. By shifting this body position information sequence by one portion, the current (most recent) body position information sequence is put into a storable state. Next, at S2, the CPU 34 acquires the output values of all the pressure detectors 32 of the pressure sensor 18.

Figure 7:
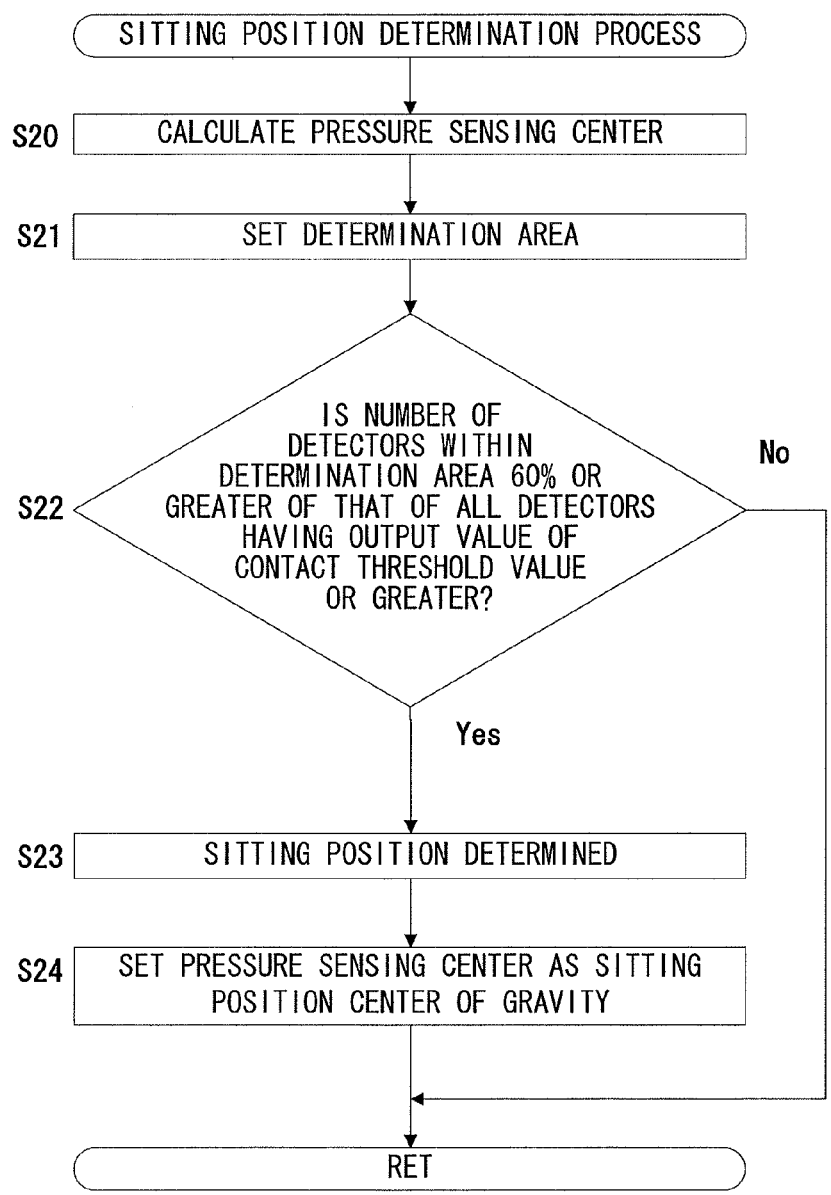
FIG. 7 is a flow chart of a sitting position determination process.
Figure 8:
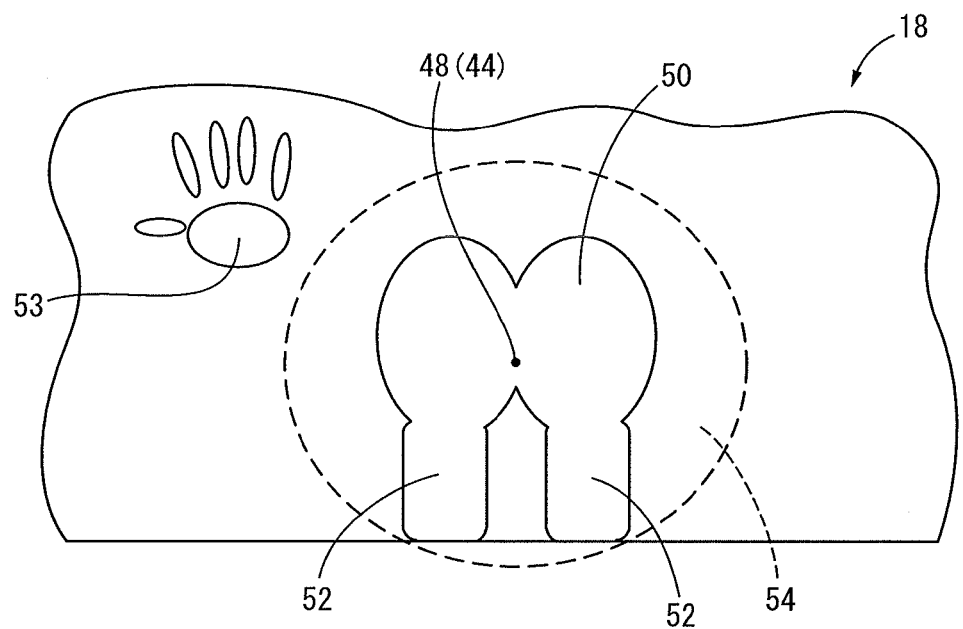
FIG. 8 is an explanatory diagram showing a contact surface of a human body on the pressure sensor when in a sitting position.

Next, at S3, the CPU 34 executes the sitting position determination process. FIG. 7 shows an example of the sitting position determination process. First, at S20, the CPU 34 calculates a pressure sensing center 48 schematically shown in FIG. 8. FIG. 8 schematically shows the human body contact surface on the pressure sensor 18 when in the sitting position, and in the drawing, code number 50 indicates buttocks of the user, and code number 52 indicates femurs of the user. In the drawing, code number 53 indicates a right hand of the user. The pressure sensing center 48 is sufficient as long as it is possible to roughly specify the center part of the region for which pressure is detected with the pressure sensor 18, and with this embodiment, the gravity center of the plurality of pressure detectors 32 having an output value of a preset contact threshold value or greater is calculated. Also, the contact threshold value is a value that can be acknowledged when something is significantly contacting the pressure detectors 32, and can be set freely to any value for identifying the pressure detectors 32 used significantly for sitting position determination. For example, with this embodiment, this is set to 1.6 mmHg.

Then, at S20, the CPU 34 calculates the center of gravity position as the coordinate value $(C_{px}, C_{py})$ of the pressure detector 32 based on the formula below, and stores that in the RAM 38. With the formula below, when any of the pressure detectors 32 $(x, y)$ is i, the output value of that pressure detector 32 is expressed as $p_i$, the x coordinate value as $x_i$, and the y coordinate value as $y_i$. Also, the total count of all the pressure detectors 32 $(x, y)$ is expressed as N, and the contact threshold value as t.

$$Cpx = \frac{\sum_{i=1}^{N}(Pi \times Xi)}{\sum_{i=1}^{N} Pi},$$

$$Cpy = \frac{\sum_{i=1}^{N}(Pi \times Yi)}{\sum_{i=1}^{N} Pi}$$

Note that when $Pi < t$, $Pi = 0$

As the pressure sensing center 48, it is also possible to use the area center of the region for which pressure of a contact threshold value or greater is detected with the pressure sensor 18. The area center can be calculated based on the formula below for example as the coordinate value ($C_{ax}$, $C_{ay}$) of the pressure detectors 32. With the formula below, the number of pressure detectors 32 ($x$, $y$) having an output value of the contact threshold value or greater is expressed as n. Working in this way, the calculation process is simplified, and it is possible to perform determination more rapidly.

$$Cax = \frac{\sum_{i=1}^{n} Xi}{n},$$

$$Cay = \frac{\sum_{i=1}^{n} Yi}{n}$$

[Formula 2]

Next, at S21, the CPU 34 sets a designated radius, circular determination area 54 with the pressure sensing center 48 shown in FIG. 8 as the center. The radius of the determination area 54 can be set freely considering the overall size of the pressure sensor 18, the arrangement pitch of the pressure detectors 32 or the like, but with this embodiment, the coordinate value of the pressure detector 32 is 3.

Then, at S22, the CPU 34 determines whether or not the number of pressure detectors 32 positioned within the determination area 54 is 60% or greater of the number of pressure detectors 32 for which pressure of the contact threshold value or greater was detected for the overall pressure sensor 18. When it is 60% or greater (S22=Yes), the CPU 34 determines at S23 that the current posture of the user is the sitting position, and at S24, after setting the pressure sensing center 48 as the sitting position center of gravity 44 shown in FIG. 8, ends the sitting position determination process. When not 60% or greater (S22=No), the CPU 34 ends the sitting position determination process. In this way, with this embodiment, the sitting position determination means is constituted including the data processing device 30 and S3.

As shown in FIG. 6, after ending the sitting position determination process (S3), at S4, when the determination results of the sitting position determination process (S3) was not the sitting position (S4=No), the CPU 34 ends the process. When the determination results of the sitting position determination process (S3) was the sitting position (S4=Yes), at S5, the CPU 34 sets the sitting position to the current (most recent) body position information sequence, and at S6, stores the coordinates ($x_1$, $y_1$) of the sitting position center of gravity 44 obtained with the setting position determination process (S3) in the RAM 38.

With the sitting position center of gravity 44, instead of using the pressure sensing center 48 obtained with the sitting position determination process (S3), for example, it is also possible to find the position for which the output total value included within the pressure detectors 32 group of a designated n rows and m columns is maximum, and use the intersection point of the diagonals of the rectangle of n rows and m columns at that position as the coordinates for the sitting position center of gravity 44 ($x_1$, $y_1$).

Next, at S7, the CPU 34 determines whether or not there is even one sitting position from the body position information sequence of the past 10 seconds not including the current time. When there was no sitting position (S7=No), at S8, the CPU 34 stores the coordinates of the stored sitting position center of gravity 44 ($x_1$, $y_1$) as the initial position ($x_0$, $y_0$) of the sitting position center of gravity 44, and also returns the continuous sitting position time to 0 and ends processing. When there was a sitting position (S7=Yes), after adding 1 for the continuous sitting position time at S9, at S10, the CPU 34 determines whether or not the movement volume |r| of the sitting position center of gravity 44 is the movement volume during bed-leaving or greater preset as the typical movement volume of the sitting position center of gravity assumed when attempting to leave bed, as well as whether or not the continuous sitting position time is a preset t0, which is 5 seconds, or less. The movement volume |r| of the sitting position center of gravity 44 is calculated based on the following formula as the distance from ($x_0$, $y_0$) to ($x_1$, $y_1$). Of course, for |r|, it is good if it is possible to compare with the movement volume during bed-leaving, so it is also possible to compare |r|$^2$ with the square value of the movement volume during bed-leaving without extracting their square roots.

$$|r| = \sqrt{(x_1-x_0)^2 + (y_1-y_0)^2}$$ [Formula 3]

When the movement volume |r| of the sitting position center of gravity 44 is the movement volume during bed-leaving or greater, and the continuous sitting position time is 5 seconds: t0 or less (S10=Yes), the CPU 34 determines that this is bed-leaving behavior, and at S11, makes a nurse call. With the nurse call, for example, through an electric line connected to the data processing device 30, a warning sound is rung or a warning lamp is displayed at a nurse station separated from the room in which the bed 12 is placed, and notification is given to a caregiver in the nurse station that the user is in the process of leaving the bed. After the nurse call (S11) ends, the CPU 34 ends processing.

Meanwhile, when the movement volume |r| of the sitting position center of gravity 44 was not the movement volume during bed-leaving or greater, or when the continuous sitting position time was not 5 seconds: t0 or less (S10=No), at S12, the CPU 34 determines whether or not the movement volume |r| of the sitting position center of gravity, except for slight movements, is a preset minimum movement volume or greater for which it is possible to determine that there is significant movement, and also determines whether or not the bed-leaving expectation position ($x_p$, $y_p$) shown in FIG. 5 is positioned within the bed-leaving range 46. The bed-leaving expectation position ($x_p$, $y_p$) is the intersection point of the movement vector: r from the initial position ($x_0$, $y_0$) of the sitting position center of gravity 44 toward the current position ($x_1$, $y_1$) and the bed-leaving range 46. The bed-leaving range 46 is the range of the edge of the bed assumed that the user will pass through when leaving the bed indicated by a bold line in FIG. 5, and with this embodiment, the range of (0, 0) to (C, E) of the straight line extending over side 1 to side 3 of the bed 12 which is the foot side region of the bed 12 is used as the bed-leaving range 46. For E, any value of 0 to R is set.

The bed-leaving expectation position $(x_p, y_p)$ for which the movement vector: r of the sitting position center of gravity 44 and the side 1 to side 3 cross are shown respectively hereafter in Formula 4 through Formula 6 for side 1 to side 3. With this embodiment, side 4 of the bed 12 is outside the bed-leaving range 46, but the bed-leaving expectation position $(x_p, y_p)$ for which the movement vector of the sitting position center of gravity 44 crosses side 4 is expressed by Formula 7. Then, using these Formulas 4 to 6, the bed-leaving expectation position $(x_p, y_p)$ that is the intersection point of the movement vector: r of the sitting position center of gravity 44 and side 1 to side 3 is found, and a determination is made of whether or not the obtained bed-leaving expectation position $(x_p, y_p)$ exists within the bed-leaving range 46.

$$\left(0, -\frac{x_0}{x_r}y_r + y_0\right) \quad \text{[Formula 4]}$$

Note that $x_r = x_1 - x_0$, $y_r = y_1 - y_0$ $$\left(-\frac{y_0}{y_r}x_r + x_0, 0\right) \quad \text{[Formula 5]}$$

Note that $x_r = x_1 - x_0$, $y_r = y_1 - y_0$ $$\left(C, -\frac{C - x_0}{x_r}y_r + y_0\right) \quad \text{[Formula 6]}$$

Note that $x_r = x_1 - x_0$, $y_r = y_1 - y_0$ $$\left(\frac{R - y_0}{y_r}x_r + x_0, R\right) \quad \text{[Formula 7]}$$

Note that $x_r = x_1 - x_0$, $y_r = y_1 - y_0$

When the movement volume: |r| of the sitting position center of gravity 44 is a minimum movement volume or greater, and the bed-leaving expectation position $(x_p, y_p)$ is within the bed-leaving range 46 (S12=Yes), the CPU 34 determines that this is bed-leaving behavior, and at S11, ends the process after a nurse call is performed. Meanwhile, when the movement volume: |r| of the sitting position center of gravity 44 is not the minimum movement volume or greater, or the bed-leaving expectation position $(x_p, y_p)$ is not within the bed-leaving range 46 (S12=No), the CPU 34 regards this as there not being bed-leaving behavior, and ends the process. As described above, with this embodiment, the bed-leaving behavior detection step is constituted including S10 and S12, and the bed-leaving behavior detection member is constituted including the data processing device 30, S10, and S12. Also, the notification member is constituted including the data processing device 30 and S11.

With this embodiment, the user sitting position is detected, and when the movement volume of the sitting position center of gravity 44 exceeds a preset movement volume during bed-leaving, or when the sitting position center of gravity 44 moves toward the bed-leaving range 46, this is detected as bed-leaving behavior connected to bed-leaving by the user. By doing this, it is possible to perform a nurse call before complete bed-leaving by the user from the bed 12. In addition to that, by focusing on the movement volume and movement direction of a user in the sitting position, it is possible to avoid having a nurse call only when the user has simply sat up, and possible to reduce false alarms.

Figure 9:
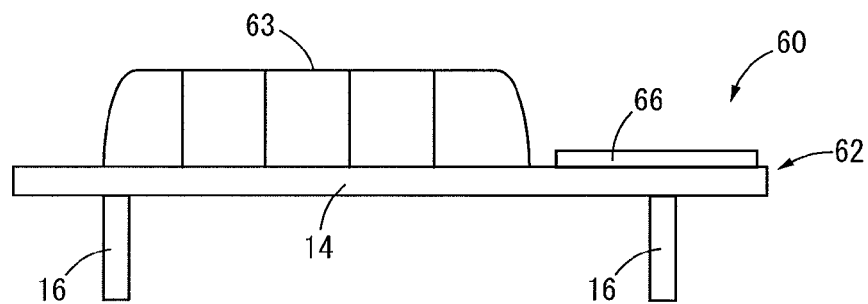
FIG. 9 is a side view of a bed equipped with a bed-leaving sensor of a second embodiment of the present invention.
Figure 10:
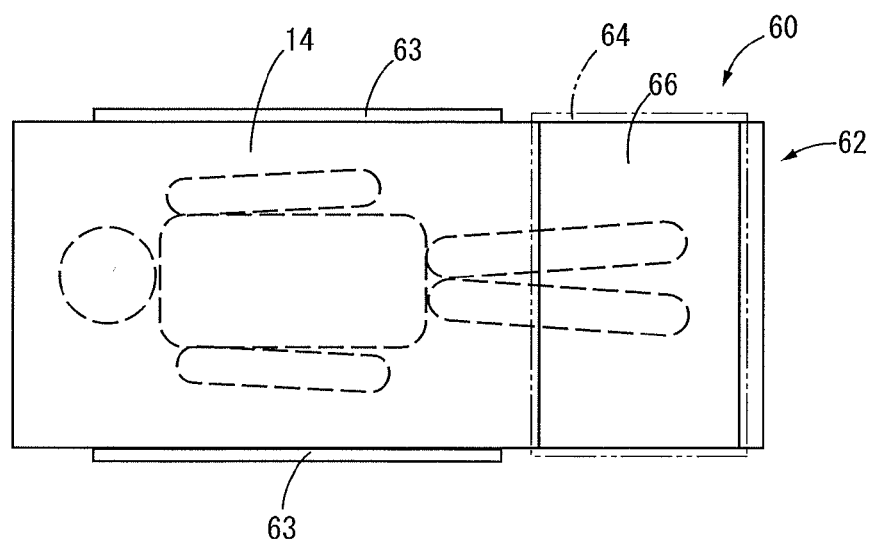
FIG. 10 is a top view of the bed shown in FIG. 9.

Next, FIG. 9 and FIG. 10 show a bed 62 as the bed equipped with a bed-leaving sensor 60 as a second embodiment of the present invention. With the description below, members and parts constituted in the same manner as the first embodiment are given the same code number as those for the first embodiment in the drawings, and thus a description is omitted.

The bed 62 of this embodiment has railings 63, 63 to prevent falling provided at both sides at which the user's torso is positioned. By doing this, with the bed 62, it is possible to leave the bed from a foot side region 64 at which the railings 63, 63 are not provided, and when the user gets down from the bed 62, he leaves the bed from the foot side region 64. In this way, with this embodiment, the bed-leaving possibility region for which it is possible for the user to get down from the bed 62 is set to be only the foot side region 64, and the bed-leaving expectation region assumed to be the sitting position when the user is leaving the bed is set to the foot side region 64.

Figure 11:
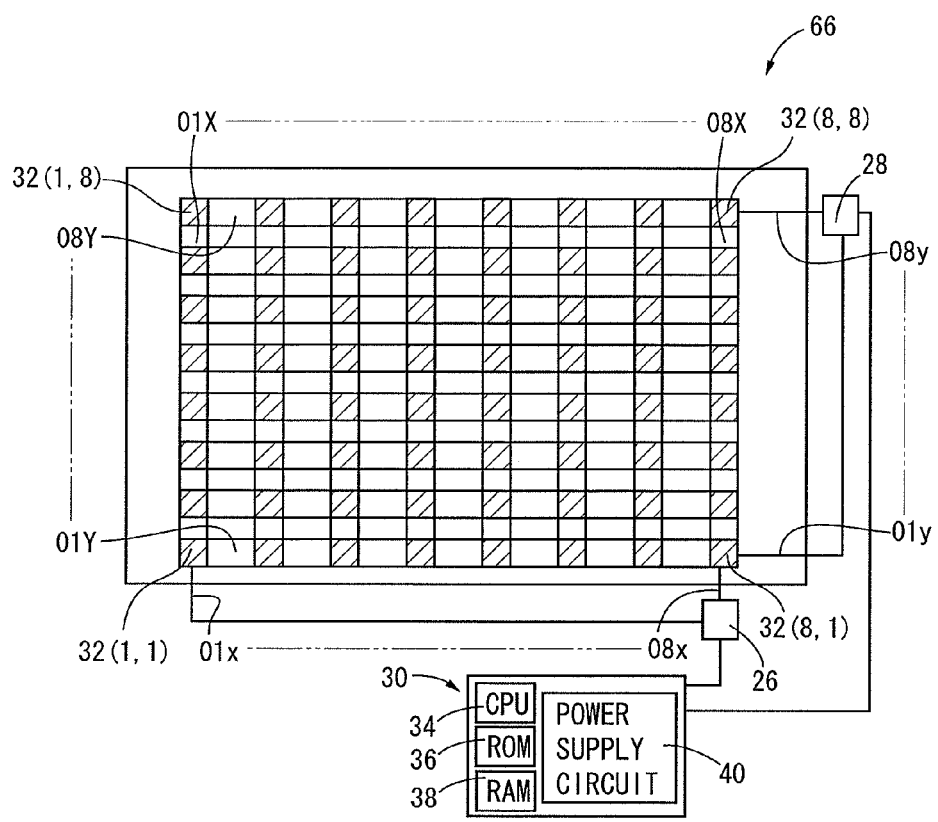
FIG. 11 is a top view of a pressure sensor provided on the bed shown in FIG. 10.

Then, a pressure sensor 66 is arranged at the foot side region 64 of the bed 62. As shown in FIG. 11, with the pressure sensor 66 of this embodiment, other than the point that the size is different from the pressure sensor 18 of the first embodiment, and the number of pressure detectors 32 is different, the constitution is the same as that of the pressure sensor 18. The pressure sensor 66 has a size corresponding to the foot side region 64, and is arranged only in the foot side region 64, and a total of 64 (=8×8) pressure detectors 32 are provided. Also, the foot part of the user on the bed 62 is made to be placed on the pressure sensor 66. The entire surface of this pressure sensor 66 is used as the sitting position determination region for determining the sitting position of the user.

Figure 12:
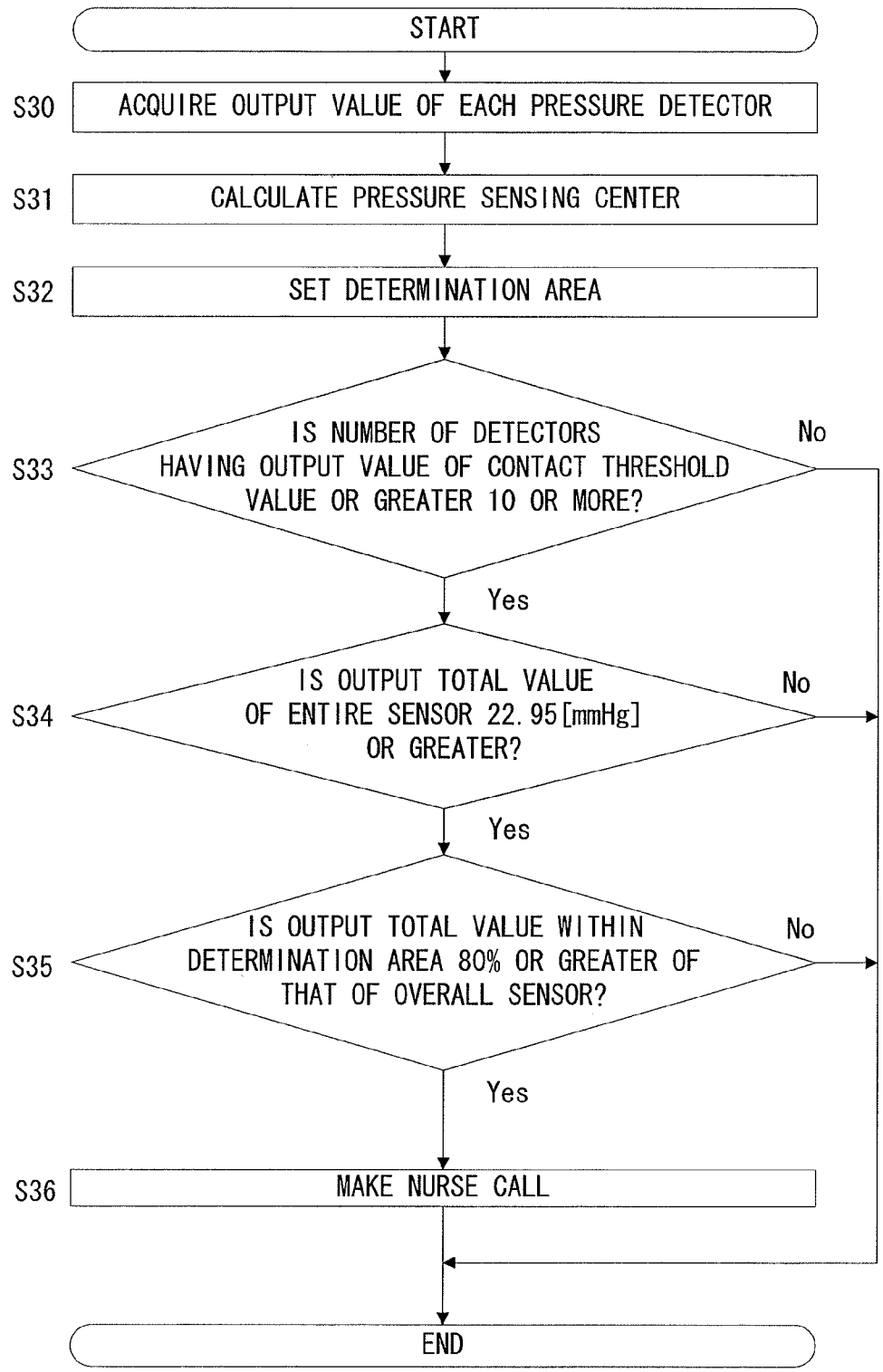
FIG. 12 is a flow chart showing a bed-leaving detection method of a second embodiment of the present invention.

Next, in FIG. 12, with the data processing device 30 of the bed-leaving sensor 60 of this embodiment, a second embodiment of the present invention is shown as the bed-leaving detection method executed by the CPU 34. First, at S30, the CPU 34 acquires the output values of all the pressure detectors 32 of the pressure sensor 66.

Figure 13:
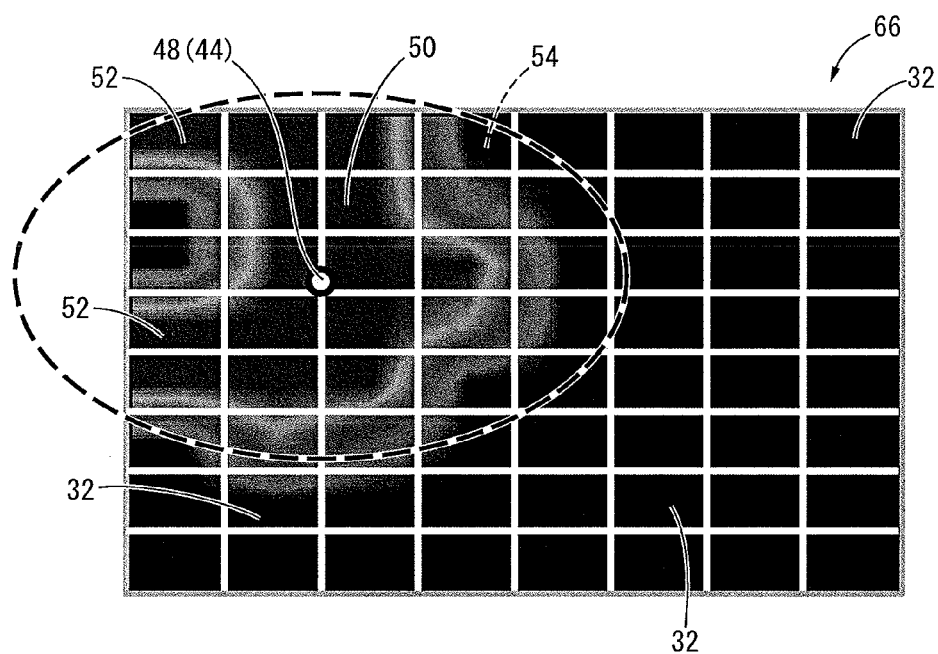
FIG. 13 is an explanatory drawing showing the pressure distribution of the sitting position during bed-leaving behavior.

Next, at S31, the CPU 34 calculates the pressure sensing center 48 shown in FIG. 13. FIG. 13 shows the actual pressure distribution when the user is in a sitting position on the pressure sensor 66. In FIG. 13, the light colored region is the region in which pressure is detected, and the pressure becomes larger as it approaches the pressure sensing center 48. Then, at S31, the CPU 34 calculates the gravity center based on the Formula 1 or the area center based on the Formula 2 as the pressure sensing center 48, and stores that in the RAM 38.

Next, at S32, the CPU 34 sets the designated radius circular determination area 54 that uses as its core the pressure sensing center 48 shown together in FIG. 13. The radius of the determination area 54 can be set freely taking into consideration the overall size of the pressure sensor 66, the arrangement pitch of the pressure detectors 32 or the like, but with this embodiment, the coordinate value of the pressure detector 32 is 3.

Next, at S33, the CPU 34 determines whether or not the breadth of the region having an output value of the preset contact threshold value or greater is a designated value or greater, specifically, whether or not the number of pressure detectors 32 having the output value of the contact threshold value or greater is 10 or more, and when it is 10 or more (S33=Yes), the process of S34 and thereafter is executed, whereas if it is not 10 or more (S33=No), the process is ended.

Next, at S34, the CPU 34 determines whether or not the total of the output values of the pressure detectors 32 of the entire pressure sensor 66 is a designated threshold value (with this embodiment, 22.95 mmHg) or greater. When the total of the output values is the threshold value or greater (S34=Yes), the process of S35 and thereafter is executed, and when the total of the output values is not the threshold value or greater (S34=No), the process ends.

Furthermore, at S35, the CPU 34 determines whether or not the ratio of the output total value of the pressure detectors 32 positioned within the determination area 54 occupying the output total value of the pressure detectors 32 of the overall pressure sensor 66 is a designated threshold value (with this embodiment, 80%) or greater. When it is the threshold value or greater (S35=Yes), the user sitting position is detected in the foot side region 64, this is regarded as bed-leaving behavior being performed by the user, and at S36, a nurse call is performed, and the process ends. Meanwhile, when it is not the threshold value or greater (S35=No), this is regarded as not having bed-leaving behavior by the user, so a nurse call is not performed, and the process ends. In this way, with this embodiment, the sitting position detection step and the bed-leaving behavior detection step are constituted including S31 to S35, and the sitting position detection member and the bed-leaving behavior detection member are constituted including the data processing device 30 and S31 to S35. Also, the notification member is constituted including the data processing device 30 and S36.

With this embodiment, the pressure sensor 66 is arranged only at the foot side region 64 as the bed-leaving possibility region. By doing this, it is possible to make the pressure sensor 66 more compact, and possible to ensure good sleep comfort for the user. Also, by having the pressure sensor 66 arranged in the foot side region 64 which is a region separated from the railings 63, 63 of the bed 62, when leaving the bed, the user always has a sitting position on the pressure sensor 66, and it is possible to reliably detect the sitting position of the user when leaving the bed.

Then, when the user sitting position is detected at the foot side region 64, this is determined to be bed-leaving behavior. By doing this, it is possible to distinguish from simply a sitting position, and to determine the bed-leaving behavior with even better precision, and also possible to perform a nurse call before the user leaves the bed 62. In particular, with the pressure sensor 66, by setting the determination area 54 in the periphery of the pressure sensing center 48 of the region for which pressure is detected, and detecting the sitting position of the user based on the size of the determination area 54 or the ratio occupied of the overall pressure sensor 66 or the like, it is possible to detect the sitting position with good precision without depending on a fixed direction of the device itself.

Above, we gave a detailed description of a plurality of embodiments of the bed-leaving sensor and the bed-leaving detection method of the present invention, but the present invention is not limited to these specific notations. For example, the bed-leaving expectation region or the sitting position determination region for which the sitting position is detected can be set freely considering the bed arrangement environment, the assumed movement at the time the user leaves the bed or the like, and in a case such as when the bed is arranged along a building wall, it is also possible to set the bed-leaving expectation region or the sitting position determination region from the head side of the outer peripheral part on the opposite side to the wall toward the foot side, or the like. Also, the bed-leaving expectation region and the sitting position determination region can be set to the entire surface of the pressure sensor, or can be set to a region of a portion of the pressure sensor. For example, it is also possible to have the pressure sensor arranged on the entire surface of the bed while also setting the bed-leaving expectation region or the sitting position determination region only in the foot side region of the pressure sensor.

Also, the specific values of the threshold values or the like shown with each of the embodiments can be set as appropriate considering the physique of the user, the size of the bed and the pressure sensor, the number of pressure detectors provided in the pressure sensor and the like, and it is not limited to the specific numerical values in the embodiments. Therefore, for example, the contact threshold value can be made to be changeable for each user according to the user's weight or the like.

What is claimed is:

1. A bed-leaving sensor for detecting bed-leaving by a user on a bed, comprising:
   a sitting position detection member that detects a sitting position of the user based on a detection value of a pressure sensor arranged on the bed; and
   a bed-leaving behavior detection member that detects bed-leaving behavior of the user with the following as a condition: (i) the sitting position being detected within a preset bed-leaving expectation region, together with (ii) a movement volume of a sitting position center of gravity which is a center of gravity of the sitting position exceeding a given threshold value within a given time, and/or (iii) the sitting position center of gravity moving toward a preset bed-leaving range,
   wherein the sitting position detection member sets a determination area in a periphery of a pressure sensing center of a region in which pressure of a given contact threshold value or greater is detected within a preset sitting position determination region on the pressure sensor, and the sitting position is detected when a breadth of a region in which the pressure of the contact threshold value or greater is detected within the determination area is a designated value or greater.

2. The bed-leaving sensor according to claim 1, wherein the bed-leaving expectation region is set to be a foot side region on the bed.

3. The bed-leaving sensor according to claim 1, wherein the pressure sensor is arranged only at a bed-leaving possibility region on the bed.

4. The bed-leaving sensor according to claim 1, wherein the sitting position detection member detects the sitting position further if a ratio of a total pressure detected within the determination area occupying a total pressure detected within the sitting position determination region is a designated value or greater, and if the total pressure detected within the sitting position determination region is a designated value or greater.

5. The bed-leaving sensor according to claim 4, wherein the pressure sensing center is a center of gravity of the region in which the pressure of the contact threshold value or greater is detected with the pressure sensor.

6. The bed-leaving sensor according to claim 4, wherein the pressure sensing center is an area center of the region in which the pressure of the contact threshold value or greater is detected with the pressure sensor.

7. The bed-leaving sensor according to claim 1, further comprising a notification member for notifying that the bed-leaving behavior of the user has been detected.

8. A bed-leaving detection method for detecting bed-leaving by a user on a bed, comprising:

a sitting position detection step for detecting a sitting position of the user based on a detection value of a pressure sensor arranged on the bed; and a bed-leaving behavior detection step for detecting bed-leaving behavior of the user with the following as a condition: (i) the sitting position being detected within a preset bed-leaving expectation region, together with (ii) a movement volume of a sitting position center of gravity which is a center of gravity of the sitting position exceeding a given threshold value within a given time, and/or (iii) the sitting position center of gravity moving toward a preset bed-leaving range, wherein with the sitting position detection step, a determination area is set in a periphery of a pressure sensing center of a region in which pressure of a given contact threshold value or greater is detected within a preset sitting position determination region on the pressure sensor, and the sitting position is detected when a breadth of a region in which the pressure of the contact threshold value or greater is detected within the determination area is a designated value or greater.

9. The bed-leaving detection method according to claim 8, wherein a foot side region on the bed is set as the bed-leaving expectation region.

10. The bed-leaving detection method according to claim 8, wherein with the sitting position detection step, the sitting position is detected further if a ratio of a total pressure detected within the determination area occupying a total pressure detected within the sitting position determination region is a designated value or greater, and if the total pressure detected within the sitting position determination region is a designated value or greater.

* * * * *